(12) United States Patent
Kim et al.

(10) Patent No.: US 9,933,888 B2
(45) Date of Patent: Apr. 3, 2018

(54) MULTIMODAL SENSOR AND MANUFACTURING METHOD THEREOF

(71) Applicant: Soongsil University Research Consortium Techno-Park, Seoul (KR)

(72) Inventors: Do Hwan Kim, Anyang-si (KR); Youngjin Jeong, Seoul (KR); So Young Kim, Seoul (KR)

(73) Assignee: SOONGSIL UNIVERSITY RESEARCH CONSORTIUM TECHNO-PARK, Seoul (KR)

( * ) Notice: Subject to any disclaimer, the term of this patent is extended or adjusted under 35 U.S.C. 154(b) by 0 days.

(21) Appl. No.: 14/986,910

(22) Filed: Jan. 4, 2016

(65) Prior Publication Data
US 2016/0259473 A1    Sep. 8, 2016

(30) Foreign Application Priority Data

Mar. 4, 2015  (KR) .................. 10-2015-0030186

(51) Int. Cl.
*G06F 3/041* (2006.01)
*G01L 5/22* (2006.01)
(Continued)

(52) U.S. Cl.
CPC ............ *G06F 3/0416* (2013.01); *G01L 1/146* (2013.01); *G01L 5/22* (2013.01); *G01N 27/221* (2013.01);
(Continued)

(58) Field of Classification Search
CPC ...... G06F 3/0416; G06F 3/0414; G01N 27/22
See application file for complete search history.

(56) References Cited

U.S. PATENT DOCUMENTS 6,726,818 B2 * 4/2004 Cui .................. C12Q 1/004
204/403.01
2002/0006233 A1 * 1/2002 Adachi .............. G06K 9/00087
382/289
(Continued)

FOREIGN PATENT DOCUMENTS

EP          2698616 A2   2/2014
JP       2000-131012 A   5/2000
(Continued)

OTHER PUBLICATIONS

European Search Report for 15203121.7 dated Jul. 12, 2016.

*Primary Examiner* — Nicholas Lee
*Assistant Examiner* — Robert Stone
(74) *Attorney, Agent, or Firm* — Pearne & Gordon LLP

(57) ABSTRACT

A multimodal sensor includes first conductive electrodes that are arranged in parallel with one another, being spaced from one another by a certain distance, an insulating layer that is formed on the first conductive electrodes, second conductive electrodes that are formed on the insulating layer, crossing the first conductive electrodes, and are arranged in parallel with one another, being spaced from one another, and a controller that applies voltages to the first and second conductive electrodes. The controller detects capacitance formed between the first and second conductive electrodes, and senses an external temperature, intensity of a pressure or a position, to which a pressure is applied, in response to a variation of the capacitance.

14 Claims, 25 Drawing Sheets

(51) Int. Cl.
*G01L 1/14* (2006.01)
*G01N 33/00* (2006.01)
*G06F 3/044* (2006.01)
*G01N 27/22* (2006.01)

(52) U.S. Cl.
CPC ......... *G01N 27/223* (2013.01); *G01N 27/227* (2013.01); *G01N 33/0001* (2013.01); *G06F 3/044* (2013.01); *G06F 3/0414* (2013.01); *G01N 2027/222* (2013.01); *G06F 2203/0381* (2013.01); *G06F 2203/04102* (2013.01); *G06F 2203/04103* (2013.01); *G06F 2203/04106* (2013.01)

(56) References Cited

U.S. PATENT DOCUMENTS

| | | | | |
|---|---|---|---|---|
| 2005/0047633 | A1* | 3/2005 | Morguet | G06K 9/00087 382/124 |
| 2005/0155411 | A1* | 7/2005 | Rogalla | B81B 7/0061 73/31.05 |
| 2005/0180618 | A1* | 8/2005 | Black | G06F 3/03545 382/124 |
| 2006/0228723 | A1* | 10/2006 | Bradley | B01L 3/50857 435/6.11 |
| 2006/0263255 | A1* | 11/2006 | Han | B82Y 10/00 422/83 |
| 2007/0048180 | A1* | 3/2007 | Gabriel | G01N 33/497 422/400 |
| 2008/0174321 | A1* | 7/2008 | Kang | G06F 3/044 324/686 |
| 2009/0201268 | A1* | 8/2009 | Endo | G06F 3/045 345/174 |
| 2011/0057669 | A1* | 3/2011 | Xu | G06F 3/044 324/658 |
| 2011/0109583 | A1* | 5/2011 | Lee | G06F 3/044 345/174 |
| 2012/0090902 | A1* | 4/2012 | Liu | G06F 3/045 178/18.03 |
| 2013/0285970 | A1* | 10/2013 | Ahn | G06F 3/044 345/173 |
| 2013/0319840 | A1* | 12/2013 | Ku | G06F 3/044 200/600 |
| 2014/0008224 | A1* | 1/2014 | Agache | B03C 5/005 204/451 |
| 2014/0104199 | A1 | 4/2014 | Lee | |
| 2014/0309947 | A1* | 10/2014 | Gryska | G01N 27/227 702/27 |
| 2014/0327845 | A1* | 11/2014 | Yashiro | G06F 3/044 349/12 |
| 2014/0375910 | A1* | 12/2014 | Tada | G06F 3/044 349/12 |
| 2016/0042166 | A1* | 2/2016 | Kang | G06F 21/32 726/7 |

FOREIGN PATENT DOCUMENTS

| | | |
|---|---|---|
| JP | 2007-139447 A | 6/2007 |
| KR | 10-0821699 B1 | 4/2008 |
| KR | 10-2010-0035380 A | 4/2010 |
| KR | 10-2011-0042924 A | 4/2011 |
| KR | 10-2014-0062846 A | 5/2014 |
| KR | 10-2014-0074445 A | 6/2014 |
| KR | 10-1415078 B1 | 7/2014 |
| WO | 2006/040781 A2 | 4/2006 |
| WO | 2006/099518 A2 | 9/2006 |
| WO | 2011/142981 A2 | 11/2011 |
| WO | 2013/083952 A1 | 6/2013 |
| WO | 2014/175524 A1 | 10/2014 |

* cited by examiner

NO TOUCH

WATER

Water    IPA    Methanol    Chloroform    Acetone    Ethanol    n-Hexane

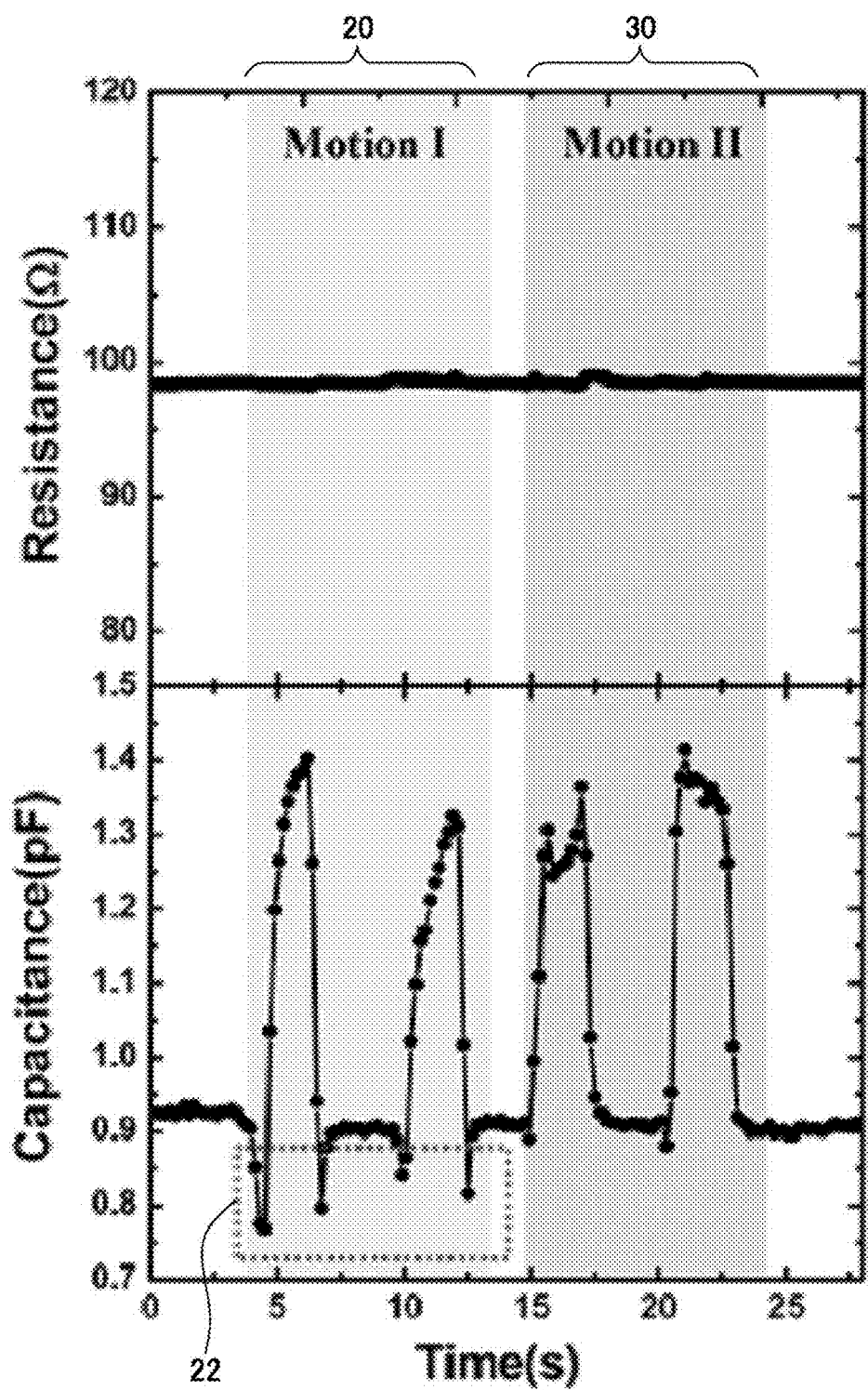

*FIG. 25*

| Solvents | Density(g/cm³) (@20°C) | Volume(μl) (@0.25g) | Dipole Moment (Debye) | ΔC/C₀ |
|---|---|---|---|---|
| Chloroform (>99.5%) | 1.492 | 167 | 1.04 | 0.002 |
| n-Hexane (95%) | 0.659 | 379 | 0 | 0.001 |
| IPA (>99.5%) | 0.785 | 318 | 1.58 | 0.014 |
| Distilled Water | 1.000 | 250 | 1.85 | 0.023 |
| Acetone (99.5%) | 0.791 | 316 | 2.88 | 0.014 |
| Methanol (99.5%) | 0.791 | 316 | 1.70 | 0.024 |
| Ethanol (99.9%) | 0.079 | 316 | 1.68 | 0.015 |

| Solvents | Density(g/cm³) (@20°C) | Volume(μl) (@0.25g) | ΔC/C₀ |
|---|---|---|---|
| Sweat solution (pH ~ 5.5) | 0.985 | 246 | 0.028 |
| Distilled Water (pH ~ 7.0) | 1.000 | 250 | 0.023 |
| Sweat solution (pH ~ 8.0) | 0.988 | 247 | 0.033 |

MULTIMODAL SENSOR AND MANUFACTURING METHOD THEREOF

CROSS-REFERENCE TO RELATED APPLICATION

This application claims the benefit of Korean Patent Application No. 10-2015-0030186 filed on Mar. 4, 2015, the disclosure of which is incorporated herein by reference.

STATEMENT REGARDING THIRD PARTY RESEARCH PROJECT

This work was supported by the Center for Advanced Soft-Electronics under the Global Frontier Project (CASE-2014M3A6A5060932) and the Basic Science Research Program (2014R1A1A1005933) of the National Research Foundation of Korea (NRF) funded by the Ministry of Science, ICT and Future Planning.

BACKGROUND

The embodiments described herein pertain generally to a multimodal sensor and a manufacturing method thereof.

Recently, there have been reports on technologies relating to electronic skin tactile sensors and chemical sensors, which can be applied to various fields such as biomonitoring systems, robot skin and haptic displays.

In conventional technologies, most tactile sensors with high sensitivity have been manufactured by using metals or inorganic substances. However, the sensors manufactured by using materials such as metals and inorganic substances are restrictive with respect to application fields. Accordingly, in order to realize electronic products such as electronic skin and flexible displays, it may be desirable to manufacture a flexible sensor by using flexible materials.

For the biomonitoring, development of a flexible electrode may be desirable to realize a tactile sensor having a flexible characteristic like human skin. However, in order to develop a flexible electrode, additional complicated processes like combination with a flexible polymer material and a patterning process are often used. Further, a sensor manufactured by these processes has a limit in size.

Meanwhile, most conventional chemical sensors sensing gas molecules are resistance-type sensors, and have detected resistance variation occurring when a chemical substance is adsorbed on a sensing layer. For the resistance-type sensors, there are technological issues regarding facilitating adsorption of a chemical substance on a sensing layer for high sensitivity of a sensor. That is, a resistance-type chemical sensor has a problem in that sensing is possible only when a sensing layer and a chemical substance directly react with each other. Accordingly, in order to enable a chemical substance to be fully adsorbed onto a sensing layer, the material for the sensing layer can be important. As such, most chemical sensors having high sensitivity use additional processes such as functionalization and combination of a sensing layer in order to improve the adsorption.

Korean Patent Application Publication No. 10-2011-0042924 (Title of Invention: Piezoresistive-Type Touch Panel, Manufacturing Method thereof, Display Device Including the Same, Touch Pad and Pressure Sensor) describes the example set forth above. Specifically, the patent application provides a method for manufacturing a piezoresistive-type touch panel, including: producing a polymer film, in which a piezoresistive film pattern with a resistance value varying depending on a pressure is embedded; producing a spacer layer to attach the spacer layer onto one side of the polymer film; and attaching a bottom substrate onto one side of the spacer layer.

Korean Patent Publication No. 10-0821699 (Title of Invention: Carbon Nanotube Chemical Sensor and Manufacturing Method thereof) also describes the example. Specifically, the patent provides a chemical sensor, which includes: an insulating layer stacked on a glass, silicon or ceramic substrate; at least one pair of electrodes stacked on a top portion of the insulating layer to face with each other; and a sensor, in which a multiple number of carbon nanotubes are diffused, forming a network structure, in a portion where the pair of electrodes are spaced from each other, wherein the multiple carbon nanotubes, and the pair of electrodes and the carbon nanotube terminals of the sensor are electrically conductive.

BRIEF SUMMARY

In view of the foregoing, example embodiments provide a method for manufacturing a multimodal sensor and an odor sensor, which simplify processes and are suitable for a large area, by using a carbon nanotube fiber. In addition, example embodiments provide a flexible multimodal sensor and odor sensor, which can be folded, bent, and twisted. However, the problems sought to be solved by the present disclosure are not limited to the above description.

In one example embodiment, a multimodal sensor is provided. The multimodal sensor includes a plurality of first conductive electrodes that are arranged in parallel with one another, being spaced from one another with a certain distance, an insulating layer that is formed on the first conductive electrodes, a plurality of second conductive electrodes that are formed on the insulating layer, cross with the first conductive electrodes, and are arranged in parallel with one another, being spaced from one another, and a controller that applies voltages to the first and second conductive electrodes, wherein the controller detects capacitance formed between the first and second conductive electrodes, and senses an external temperature, intensity of a pressure or a position, to which a pressure is applied, in response to a variation of the capacitance.

In one example embodiment, a method for manufacturing a multimodal sensor is provided. The method includes arranging a plurality of first conductive electrodes on a first substrate; arranging a plurality of second conductive electrodes on a second substrate; forming an insulating layer on the first conductive electrodes; and connecting the first and second substrates with each other, so as to make the plurality of the second conductive electrodes contact on the insulating layer, wherein the connecting of the first and second electrodes with each other is forming the first and second conductive electrodes to cross with one another.

In one example embodiment, a multimodal sensor is provided. The multimodal sensor includes first conductive electrode, an insulating layer formed on the first conductive electrode, a second conductive electrode that is formed on the insulating layer, and crosses with the first conductive electrode, and a controller that applies voltages to the first and second conductive electrodes, wherein the controller detects capacitance formed between the first and second conductive electrodes, and senses an external temperature, intensity of a pressure, or a position, to which a pressure is applied, in response to a variation of the capacitance.

In one example embodiment, a method for manufacturing a multimodal sensor is provided. The method includes forming a first conductive electrode on a first substrate in a plane shape; forming a second conductive electrode on a second substrate in a plane shape; forming an insulating layer on the first conductive electrode; and connecting the first and second substrates with each other, so as to make the second conductive electrode contact on the insulating layer, wherein the connecting of the first and second electrodes with each other is forming the first and second conductive electrodes to cross with each other.

In accordance with the example embodiments, there is an effect of simplifying processes for manufacturing a multimodal sensor and an odor sensor by using a carbon nanotube fiber. Thus, in accordance with one example embodiment suggested by the present disclosure, it is possible to manufacture a multimodal sensor and an odor sensor, which are suitable for a large area.

Further, it is possible to manufacture a flexible multimodal sensor and odor sensor, which can be folded, bent, and twisted.

In addition, the odor sensor in accordance with one example embodiment suggested by the present disclosure can detect a specific substance by using variation of a capacitance without directly reacting with a conductive electrode. Thus, there is an effect on improving the lifetime of the odor sensor.

BRIEF DESCRIPTION OF THE DRAWINGS

FIG. 24 shows an example embodiment for detecting motions by using the multimodal sensor manufactured in accordance with an example embodiment.

FIG. 25 shows a variation value of capacitance depending on change of a solvent contacting the multimodal sensor manufactured in accordance with an example embodiment.

DETAILED DESCRIPTION

Figure 1:
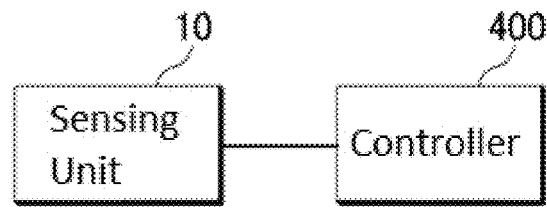
FIG. 1 shows a structure of a multimodal sensor in accordance with an example embodiment.

Hereinafter, example embodiments will be described in detail with reference to the accompanying drawings so that the inventive concepts may be readily implemented by those skilled in the art. However, it is to be noted that the present disclosure is not limited to the example embodiments but can be realized in various other ways. In the drawings, certain parts not directly relevant to the description are omitted to enhance the clarity of the drawings, and like reference numerals denote like parts throughout the whole document.

Throughout the document, the terms "connected to" or "coupled to" are used to designate a connection or coupling of one element to another element and include both a case where an element is "directly connected or coupled to" another element and a case where an element is "electronically connected or coupled to" another element via still another element. Further, the term "comprises or includes" and/or "comprising or including" used in the document means that one or more other components, steps, operations, and/or the existence or addition of elements are not excluded in addition to the described components, steps, operations and/or elements.

Hereinafter, the multimodal sensor and the manufacturing method thereof in accordance with an example embodiment are described in detail.

FIG. 1 shows a structure of the multimodal sensor in accordance with an example embodiment.

Figure 2:
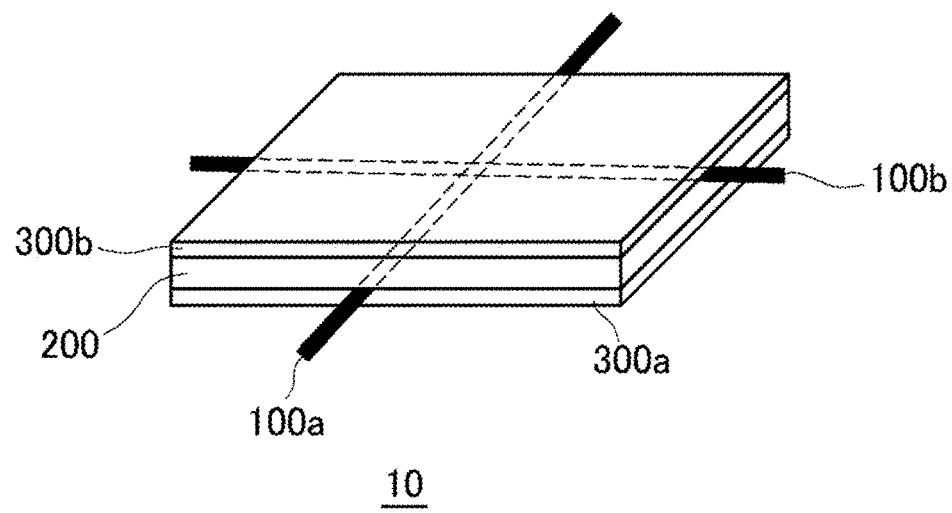
FIG. 2 shows a sensing unit of the multimodal sensor in accordance with an example embodiment.
Figure 3:
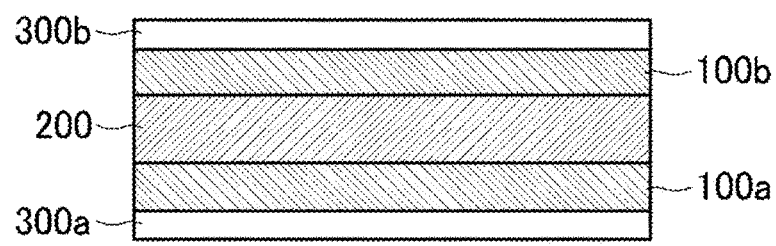
FIG. 3 shows a cross section of the sensing unit of the multimodal sensor in accordance with an example embodiment.

FIG. 2 shows a sensing unit of the multimodal sensor in accordance with an example embodiment, and FIG. 3 shows a cross section of a sensing unit of the multimodal sensor in accordance with an example embodiment.

Referring to FIG. 1, the multimodal sensor in accordance with an example embodiment includes a sensing unit 10 and a controller 400.

The sensing unit 10 includes a first conductive electrode 100a, a second conductive electrode 100b, an insulating layer 200, a first substrate 300a and a second substrate 300b as illustrated in FIG. 2 and FIG. 3.

Referring to FIG. 2 and FIG. 3, the sensing unit 10 of the multimodal sensor in accordance with an example embodiment includes the first substrate 300a, which is of a plane shape, and the second substrate 300b, which faces to the first substrate 300a and is spaced from the first substrate 300a with a certain distance. In this case, the first substrate 300a and the second substrate 300b, which are of a plane shape, protect the first conductive electrode 100a and the second conductive electrode 100b from the outside.

The first substrate 300a and the second substrate 300b may be formed of a flexible material. With respect to examples for the flexible material, an acrylic plate, a thin film, plastic, a polymer material, polydimethylsiloxane (PDMS) or others may be used. In addition, the first substrate 300a and the second substrate 300b, which are of a plane shape, may be formed of a material having elasticity.

Meanwhile, the first substrate 300a and the second substrate 300b are members, to which an external pressure is applied, and may be transformed by an external pressure. In addition, the first substrate 300a and the second substrate 300b may be restored to their original state after the application of the external pressure.

The first conductive electrode 100a may be formed on the top portion of the first substrate 300a, and the second conductive electrode 100b may be formed on the bottom portion of the second substrate 300b. In this case, the first conductive electrode 100a and the second conductive electrode 100b may be in a linear shape and arranged to cross with each other. For example, where the first conductive electrode 100a has been positioned on the top portion of the first substrate 300a along an X axis direction, the second conductive electrode 100b may be positioned in a Y axis direction vertical to the first electrode 100a.

In this case, the first conductive electrode 100a and the second conductive electrode 100b may be formed of an inorganic substance having conductivity such as a carbon nanotube fiber, a carbon nanotube film, gold, silver, copper or a conductive polymer, but is not limited thereto.

The multimodal sensor in accordance with an example embodiment includes the insulating layer 200 between the first conductive electrode 100a and the second conductive electrode 100b. In this case, the insulating layer 200 may be formed of any one of ecoflex, PDMS, or a silicon-based substance.

Figure 4:
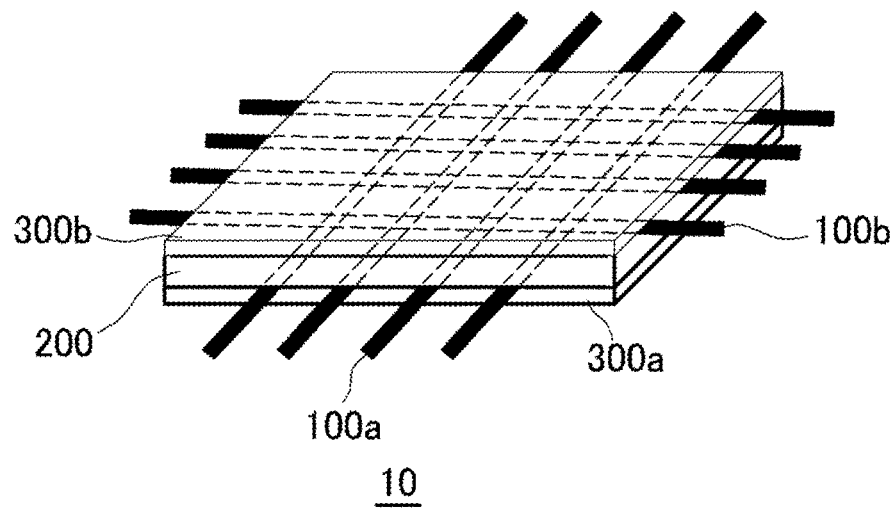
FIG. 4 shows a sensing unit of a capacitor-type multimodal sensor in accordance with another example embodiment.

FIG. 4 shows a sensing unit of a multimodal sensor in accordance with another example embodiment.

Referring to FIG. 4, the sensing unit in accordance with another example embodiment may further include a multiple number of conductive electrodes, which are formed in parallel with the first conductive electrode 100a on the top portion of the first conductive electrode 300a. Likewise, the sensing unit in accordance with another example embodiment may further include a multiple number of conductive electrodes, which are arranged in parallel with the second conductive electrode 100b on the bottom portion of the second substrate. In this case, the multiple conductive electrodes may have a linear shape and be arranged being spaced from one another with a certain distance.

Figure 5:
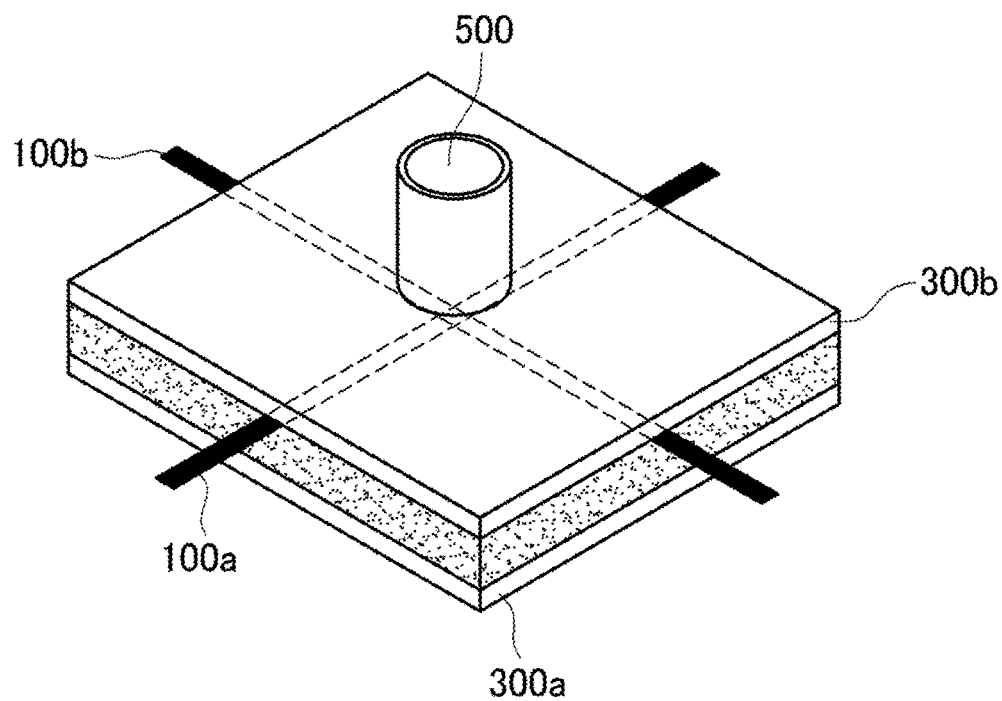
FIG. 5 shows a sensing unit of a multimodal sensor in accordance with another example embodiment.

FIG. 5 shows a sensing unit of a multimodal sensor in accordance with another example embodiment.

Meanwhile, the multimodal sensor in accordance with another example embodiment may be an odor sensor, and include a receiver 500 to detect a specific chemical substance on the first substrate 300a or the second substrate 300b, as illustrated in FIG. 5. In this case, the receiver 500 may be variously selected depending on a chemical substance to be detected.

Returning to FIG. 1, the multimodal sensor in accordance with an example embodiment includes a controller 400 inside or outside the sensor. In this case, the controller 400 applies voltages to the first conductive electrode 100a and the second conductive electrode 100b, and detects variation of a value of capacitance formed between the first conductive electrode 100a and the second conductive electrode 100b.

More specifically, when a voltage is applied to the sensing unit of the multimodal sensor in accordance with an example embodiment, capacitance is formed between the first conductive electrode 100a and the second conductive electrode 100b. A value of the capacitance varies in real time in an environment where a liquid- or gas-state chemical substance exists, when touch occurs on or a pressure is applied to the surface of the first substrate 300a or the second substrate 300b, or according to various environment changes such as external humidity change, temperature change and pressure change. In this case, the controller 400 may measure a value of the capacitance, which varies in real time, to detect external humidity change, temperature change, a position where touch occurs on the surface of the first substrate 300a or the second substrate 300b, a pressure, a chemical substance present on gas in which the multimodal sensor placed.

Although not illustrated, the controller 400 in accordance with an example embodiment includes an analog to digital converter, a signal processor and a memory unit to detect a value of the capacitance varying in real time, measure a position to be touched, or convert the detected capacitance value into physical quantities such as a pH value in response to a pressure, a temperature, humidity or a chemical substance.

In this case, the analog to digital converter may change a capacitance value detected in real time into a computer readable digital value to store the value in the memory unit.

In addition, the memory unit is one of computer storage media and may include all volatile/nonvolatile and removable/non-removable media embodied by a certain method or technology for storing information such as computer readable instruction code, a data structure, a program module or other data. For example, the storage device may include NAND flash memories such as a read only memory (ROM), a random access memory (RAM), a magnetic tape, a magnetic disk, a flash memory, an optical data storage device, a compact flash (CF) card, a secure digital (SD) card, a memory stick, a solid-state drive (SSD) and a micro SD card, and magnetic computer storage devices such as a hard disk drive (HDD).

The signal processor may convert the capacitance value into a pH value of a specific chemical substance temperature, a pressure, humidity based on a pre-stored database or look-up table. For example, the signal processor may calculate a dipole moment value matched with a capacitance variation value according to a specific chemical substance by using a look-up table, and then, detect the corresponding specific chemical substance.

When a pressure is applied to, or touch occurs in the first substrate 300a or the second substrate 300b of the multimodal sensor in accordance with an example embodiment, the signal processor may calculate x and y coordinates of the position, to which the pressure is applied, or the position where the touch occurs.

In addition, the signal processor may measure a variation quantity of capacitance in real time, and determine whether a first object touched on the first substrate 300a is identical in nature to a second object touched on the second substrate 300b.

Figure 6:
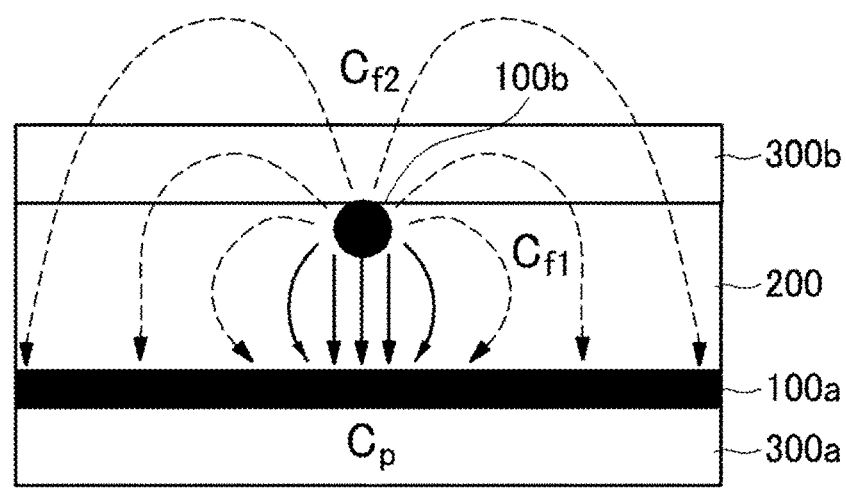
FIG. 6 shows capacitance formed in the multimodal sensor in accordance with an example embodiment.

FIG. 6 shows capacitance formed in the multimodal sensor in accordance with an example embodiment.

Figure 7:
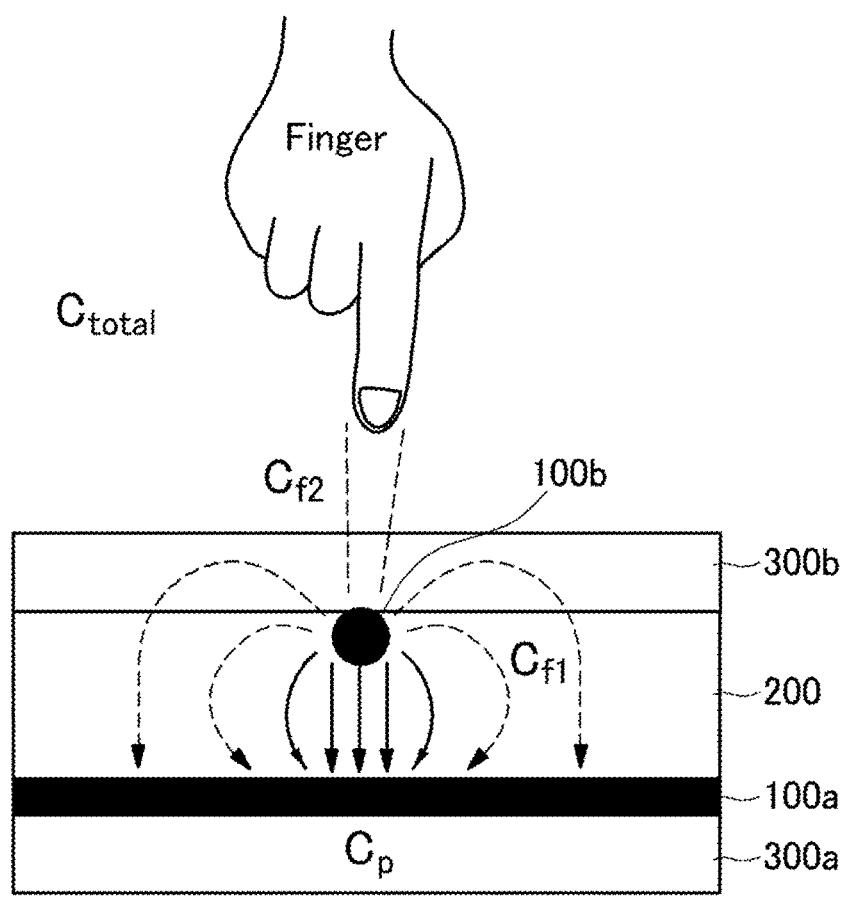
FIG. 7 shows variation of a capacitance value depending on external touch in the multimodal sensor in accordance with an example embodiment.

FIG. 7 shows variation of a capacitance value depending on external touch in the multimodal sensor in accordance with an example embodiment.

Figure 8:
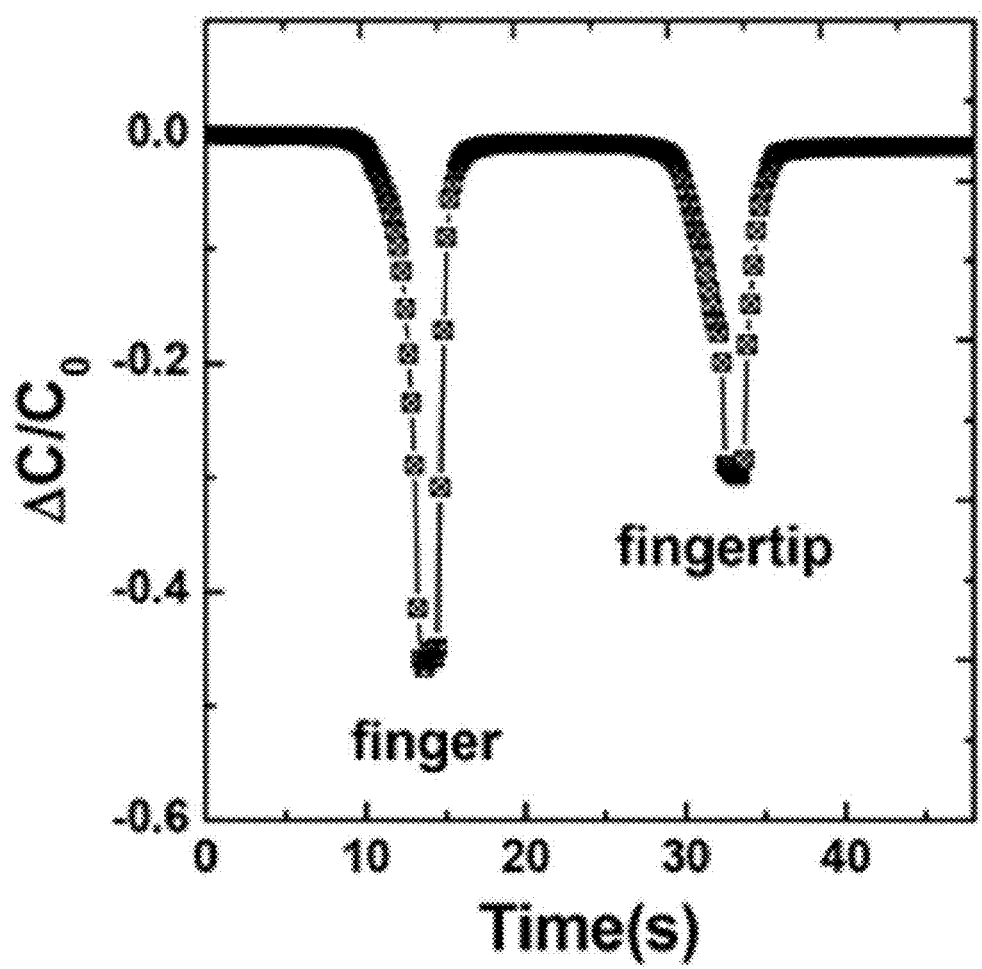
FIG. 8 is a graph for a capacitance value varying depending on external touch in the multimodal sensor in accordance with an example embodiment.

FIG. 8 is a graph for a capacitance value varying depending on external touch in the multimodal sensor in accordance with an example embodiment.

Figure 9A:
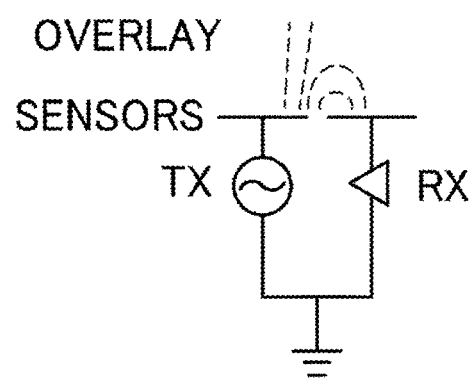
FIGS. 9A, 9B, and 9C show variation of capacitance depending on an external substance, in the multimodal sensor in accordance with an example embodiment.
Figure 9B:
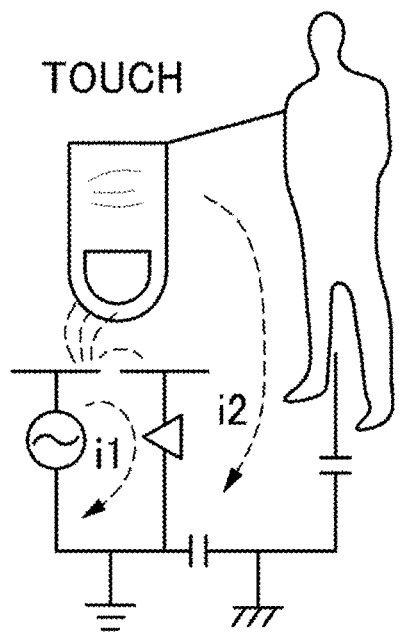
Figure 9C:
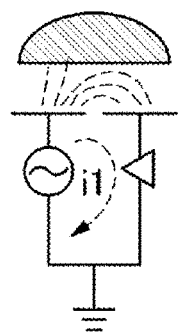

FIGS. 9A-9C show capacitance variation depending on an external substance (e.g., touch, no touch, and water) in the multimodal sensor in accordance with an example embodiment.

Referring to FIG. 6 to FIGS. 9A-9C, the sensing unit 10 of the multimodal sensor in accordance with an example embodiment includes capacitance ($C_p$) formed in the inside of the first conductive electrode 100a and the second conductive electrode 100b, capacitance ($C_{f1}$) fringed in the inside of the two electrodes and capacitance ($C_{f2}$) fringed toward the outside of the two electrodes. Accordingly, a total volume ($C_t$) of capacitance formed in the sensing unit 10 of the multimodal sensor in accordance with an example embodiment follows Formula 1.

$$C_t = C_p + C_{f1} + C_{f2}$$ [Formula 1]

When a user touches the surface of the first substrate 300a or the second substrate 300b of the multimodal sensor, the capacitance ($C_{f2}$) to be fringed outwardly is leaked through the hands of the user. As a result, the total volume ($C_t$) of the capacitance formed in the sensing unit 10 of the multimodal sensor is reduced.

Accordingly, the controller 400 detects an external temperature, a size of a pressure to be applied to the first substrate 300a or the second substrate 300b, a position to be touched, an external temperature or others through variation of a capacitance value generated between the first conductive electrode 100a and the second conductive electrode 100b.

On the other hand, as illustrated in FIG. 9C, when a specific chemical substance (e.g., water) having a dipole moment contacts the surface of the first substrate 300a or the second substrate 300b of the multimodal sensor, it results in an effect of increasing the capacitance ($C_{f2}$) to be fringed outwardly. As a result, a total volume ($C_{total}$) of the capacitance formed in the sensing unit 10 of the multimodal sensor increases.

Accordingly, the controller 400 may detect external humidity, a specific chemical substance present on or in the vicinity of the surface of the first substrate 300a or the second substrate 300b, a pH value of a specific chemical substance or others through variation of the capacitance generated between the first conductive electrode 100a and the second conductive electrode 100b. In other words, it is possible to detect a specific chemical substance without direct reaction between a chemical substance and a conductive electrode, and thus, the lifetime of the sensor can be increased.

Figure 10:
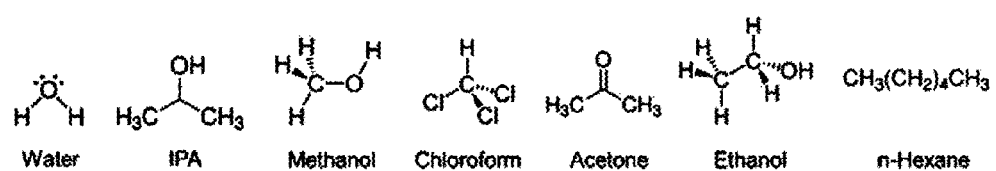
FIG. 10 shows molecular structures of chemical substances, which are assumed in an example embodiment.

FIG. 10 shows dipole moments of chemical substances, which are assumed in an example embodiment.

Figure 11:
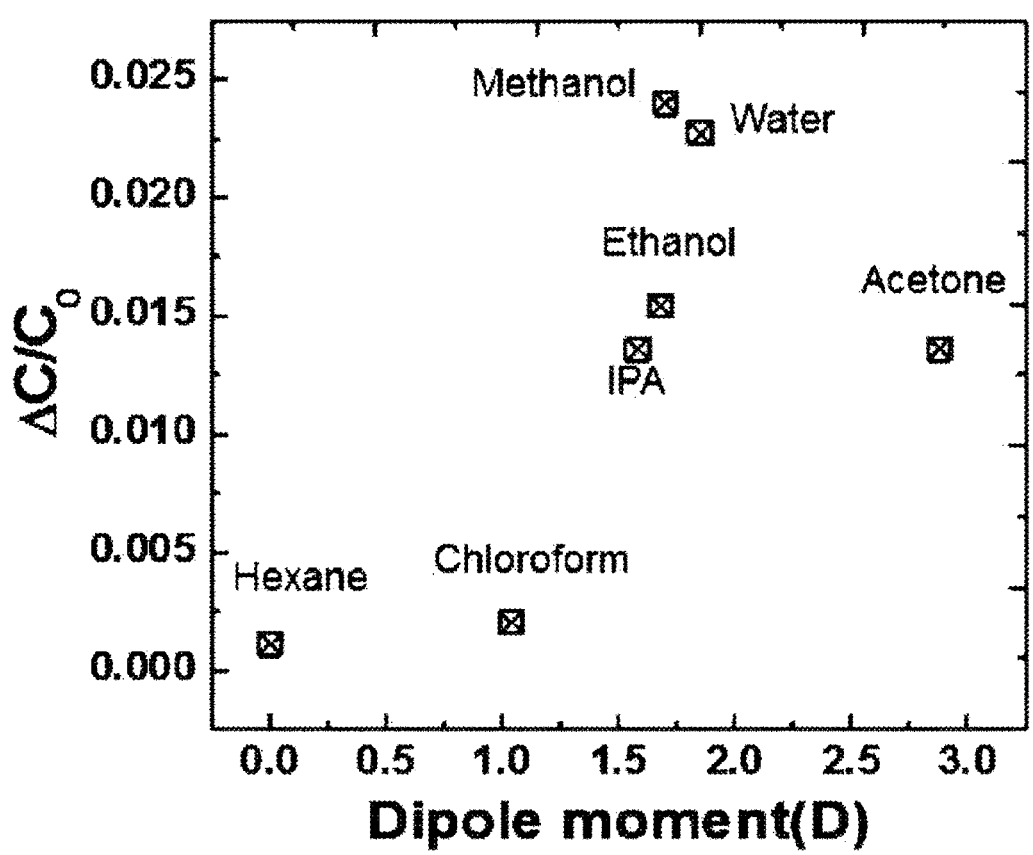
FIG. 11 is a graph for a capacitance value depending on a dipole moment value of the multimodal sensor in accordance with an example embodiment.

FIG. 11 is a graph for a capacitance value according to a dipole moment of the multimodal sensor in accordance with an example embodiment.

Referring to FIG. 10, random chemical substances have their dipole moment values, which are different from one another. Accordingly, as illustrated in FIG. 11, the multimodal sensor in accordance with an example embodiment has different capacitance variation values depending on dipole moment values of random chemical substances. Referring to FIG. 11, the tendency that as a dipole moment value of a random chemical substance increases, a capacitance variation value increases can be identified.

Figure 12A:
FIGS. 12A, 12B, 12C, 12D, 12E, and 12F depict a method for manufacturing the sensing unit of the multimodal sensor in accordance with an example embodiment.
Figure 12B:
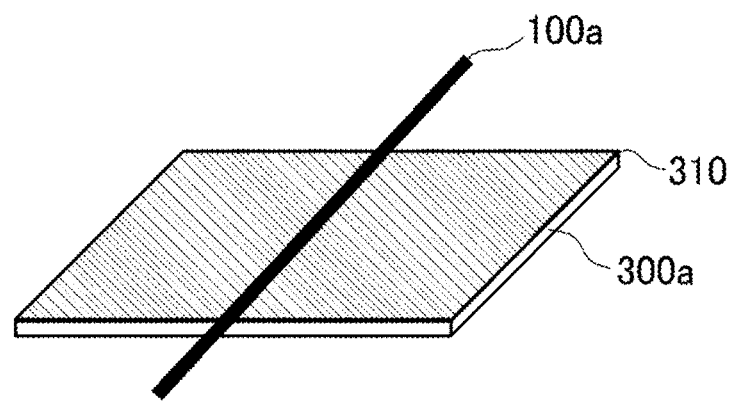
Figure 12C:
Figure 12D:
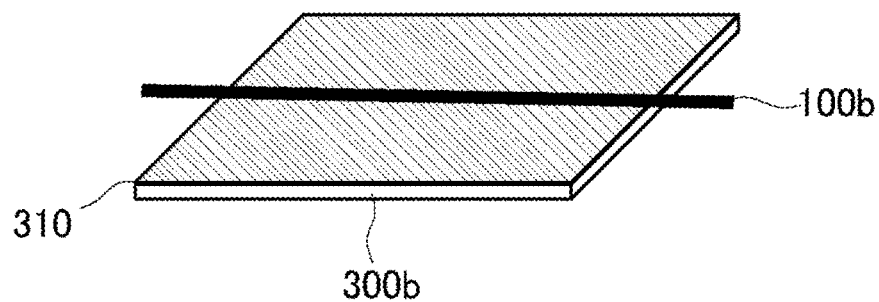
Figure 12E:
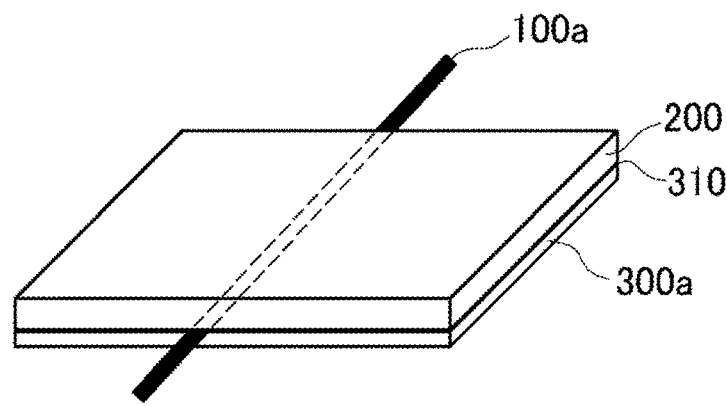
Figure 12F:
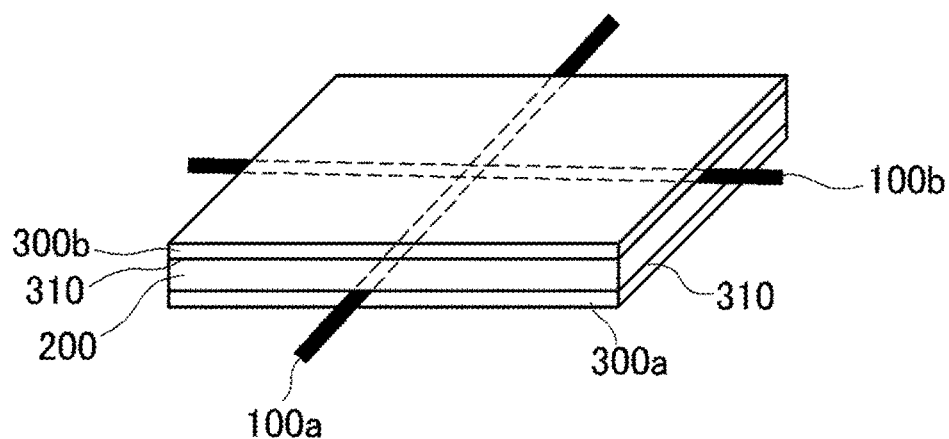

FIGS. 12-12F specifically depicts a method for manufacturing the sensing unit of the multimodal sensor in accordance with an example embodiment.

Referring to FIGS. 12A-12F, the method for manufacturing the sensing unit 10 of the multimodal sensor in accordance with an example embodiment may (FIG. 12A) prepare the first substrate 300a, and form the first conductive electrode 100a on the top portion of the first substrate 300a. For example, the method of forming the first conductive electrode 100a may (FIG. 12B) apply an adhesive layer 310 onto the first substrate 300a and arrange the linear conductive organic•inorganic material on the top portion of the adhesive layer 310 along a y axis.

Subsequently, the method for manufacturing the sensing unit 10 of the multimodal sensor in accordance with an example embodiment may (FIG. 12C) prepare the second substrate 300b, and form the second conductive electrode 100b on the top portion of the second substrate 300b. For example, like the method of forming the first conductive electrode 100a, the method of forming the second electrode 100b may (FIG. 12D) apply the adhesive layer 310 onto the second substrate 300b and arrange the conductive electrode on the top portion of the adhesive layer 310 along an x axis.

In this case, the first conductive electrode 100a and the second conductive electrode 100b may be formed of any one of organic or inorganic materials having conductivity such as a carbon nanotube fiber, a carbon nanotube film, gold, silver, copper or a conductive polymer.

In accordance with an example embodiment, the first conductive electrode 100a and the second conductive electrode 100b may be a carbon nanotube fiber.

Figure 13:
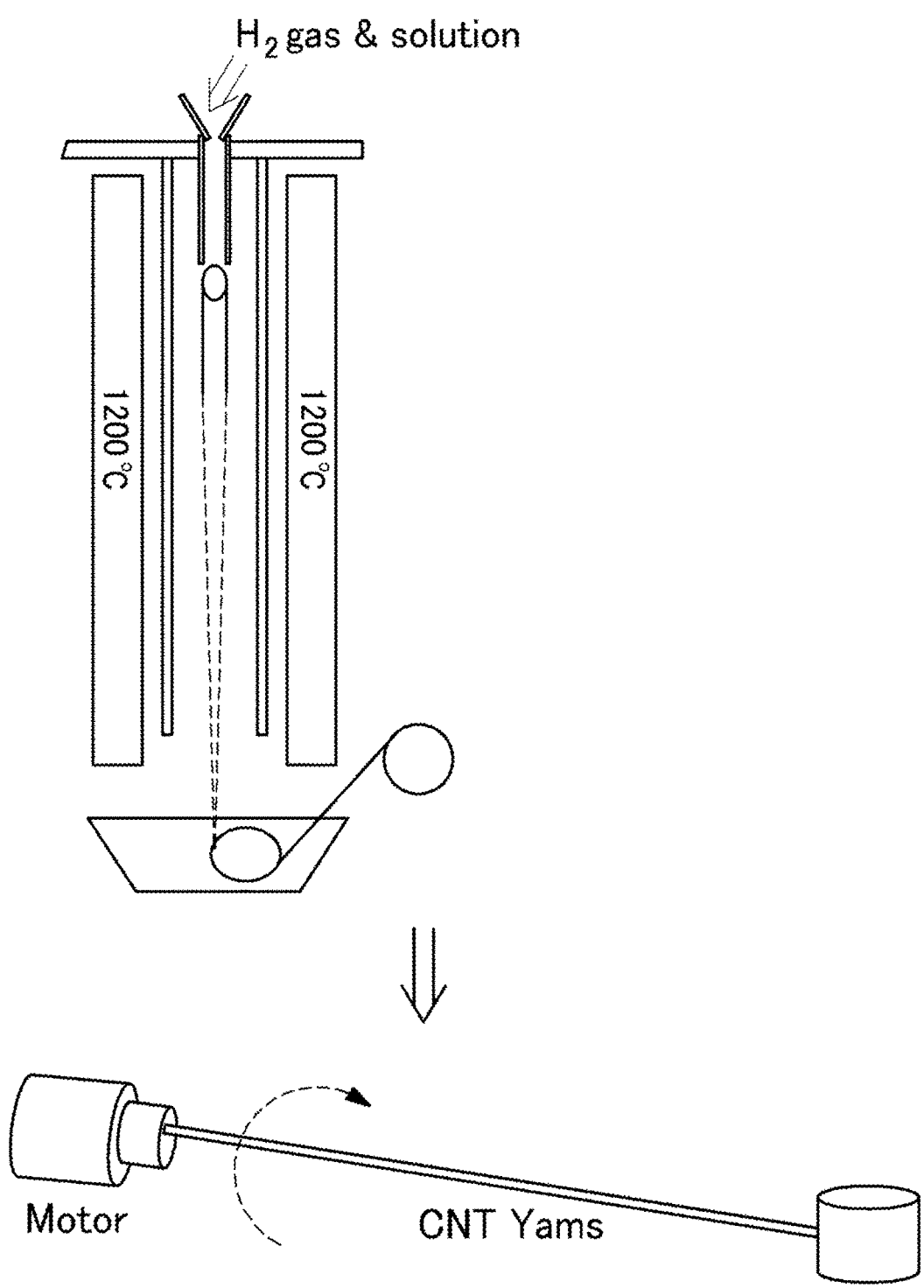
FIG. 13 shows manufacturing a carbon nanotube fiber, which forms an electrode of the multimodal sensor, in accordance with an example embodiment.

FIG. 13 shows manufacturing a carbon nanotube fiber, which forms the electrode of the multimodal sensor in accordance with an example embodiment.

In the multimodal sensor in accordance with an example embodiment, the carbon nanotube fiber, which forms the first conductive electrode 100a and the second conductive electrode 100b, may be manufactured by winding a carbon nanotube film by means of a motor as illustrated in FIG. 13. In this case, it is possible to manufacture a carbon nanotube fiber having a desired diameter according to the number of times for winding the carbon nanotube film with a motor.

Specifically, the carbon nanotube film may be prepared by heating a vertically placed quartz tube, flowing high purity hydrogen gas into the quartz tube, and supplying a small amount of a carbon nanotube synthetic solution into a vertical synthesis furnace. In this case, the carbon nanotube synthetic solution is a mixture of acetone, which is used as a carbon supply source, ferrocene, which is a catalyst precursor, thiophene, which is an activator, and polysorbate_20 for suppression of catalyst agglutination.

More specifically, once the synthetic solution is supplied into the synthesis furnace, iron is isolated from ferrocene, which is a catalyst precursor, and sulfur is isolated from thiophene, which is an activator, through heat energy. Thereafter, due to decomposition of acetone, the supplied carbons are diffused to be iron sulfide and saturated, and the carbon nanotubes begin to grow. In this case, where the solution is continuously injected, the carbon nanotubes form an aggregation, and this aggregation may be wound on a roller to manufacture the carbon nanotube film. Subsequently, a carbon nanotube fiber having a desired diameter may be manufactured by winding the carbon nanotube film with a motor.

Meanwhile, Korean Patent No. 10-2013-0044173, which was suggested by the inventor of the present disclosure, and PCT/KR2013/010289 more specifically describe the method for manufacturing the carbon nanotube fiber in accordance with an example embodiment.

Figure 14A:
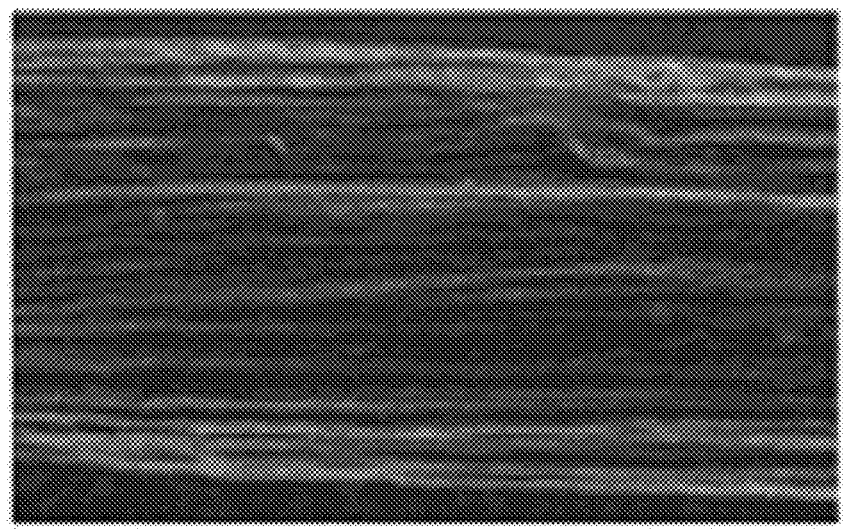
FIGS. 14A and 14B show images of a surface of the carbon nanotube fiber manufactured in accordance with an example embodiment.
Figure 14B:
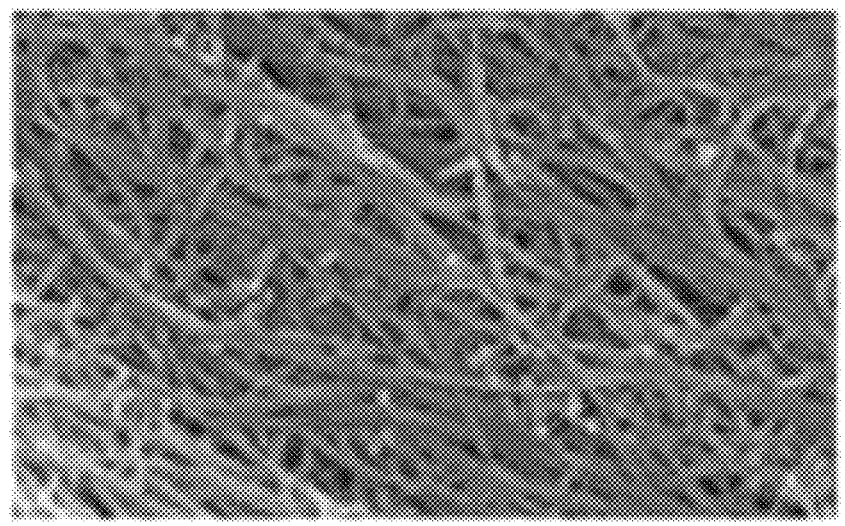
Figure 15A:
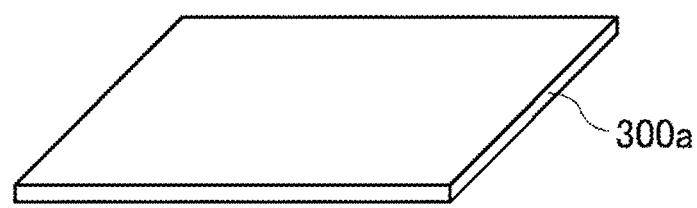
FIGS. 15A, 15B, 15C, 15D, 15E, and 15F depict a method for manufacturing the sensing unit of the multimodal sensor in accordance with another example embodiment.
Figure 15B:
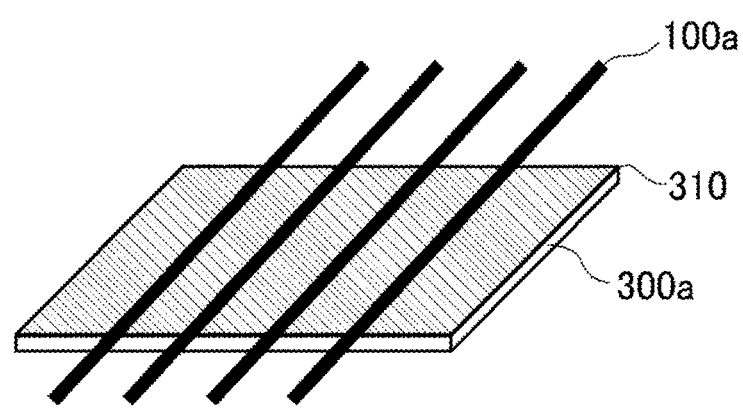
Figure 15C:
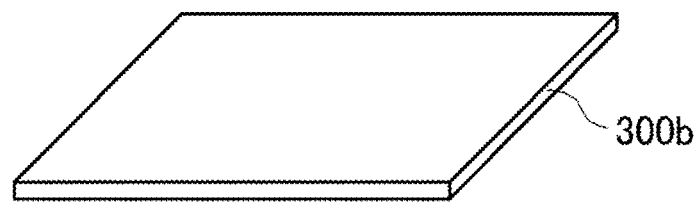
Figure 15D:
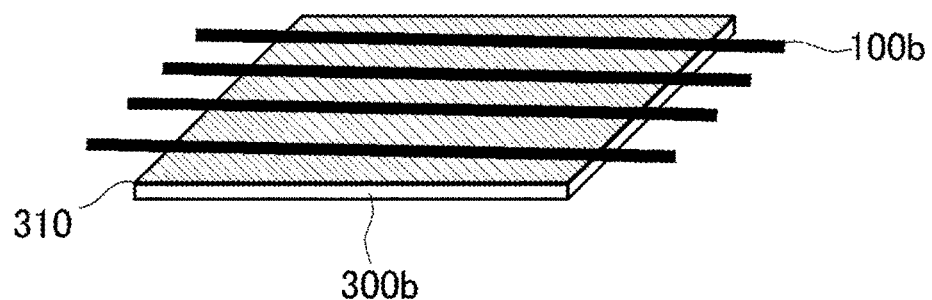
Figure 15E:
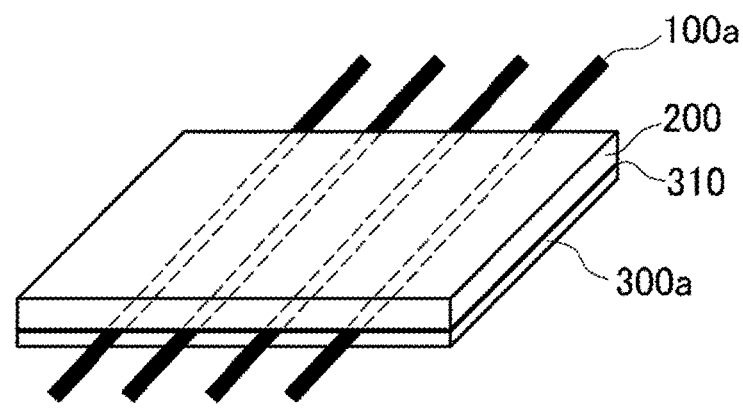
Figure 15F:
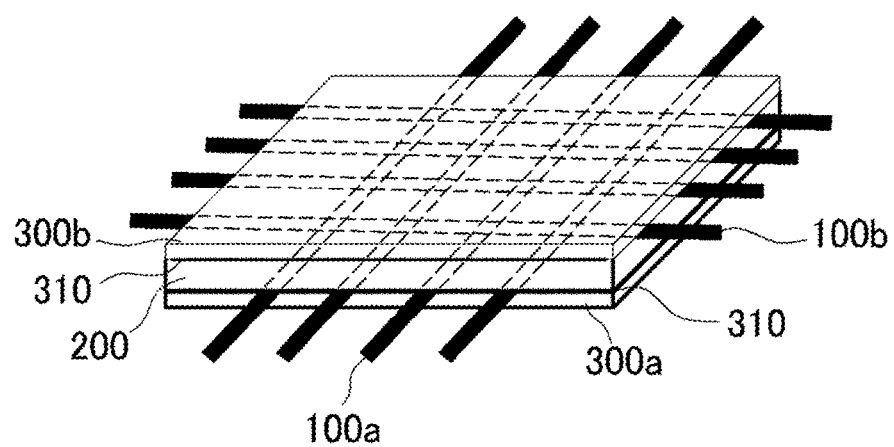

FIG. 14 shows images of a surface of the carbon nanotube fiber prepared in accordance with an example embodiment.

As illustrated in FIG. 14, the surface of the carbon nanotube fiber in accordance with an example embodiment is not even. This characteristic helps the multimodal sensor of the example embodiments to sensitively react even at a low pressure when it operates as a pressure sensor or a touch sensor, resulting in an effect of improving sensitivity of the sensor.

Returning to FIGS. 12A-F, the method for manufacturing the sensing unit 10 of the multimodal sensor in accordance with an example embodiment may (FIG. 12E) apply an insulating material on the first conductive electrode 100a to form the insulating layer 200, after forming the first conductive electrode 100a and the second conductive electrode 100b on the first substrate 300a and the second substrate 300b. In an example embodiment, the insulating material may be an ecoflex material, which is a silicon-based material having an elastic modulus, but not limited thereto.

Subsequently, (FIG. 12F) the second substrate 300b is inversed in upward, downward, rightward and leftward directions and connected with the first substrate, so as to make the insulating layer 200 formed on the top portion of the first substrate 300a and the second conductive electrode 100b formed on the top portion of the second substrate 300b next to each other.

FIGS. 15A-15F depict the method for manufacturing the sensing unit of the multimodal sensor in accordance with another example embodiment.

Meanwhile, as illustrated in FIGS. 15A-15F, the method for manufacturing the sensing unit 10 of the multimodal sensor in accordance with another example embodiment may, in the step (FIG. 15B) for manufacturing the first conductive electrode 100a on the first substrate 300a, arrange a multiple number of linear conductive electrodes to be in parallel with one another with a certain interval, so as to be in parallel with the first conductive electrode 100a, on the top portion of the adhesive layer 310 applied onto the first substrate 300a.

In addition, in the step (FIG. 15D) for manufacturing the second conductive electrode 100b on the second substrate 300b, a multiple number of linear conductive electrodes may be arranged to be in parallel with one another with a certain interval, so as to be in parallel with the second conductive electrode 100b, on the top portion of the adhesive layer 310 applied onto the second substrate 300b.

In addition, in accordance with another example embodiment, the method for manufacturing the sensing unit 10 of the multimodal sensor as illustrated in FIGS. 12A-12F and FIGS. 15A-15F may further include attaching the receiver 500 for detection of a specific chemical substance onto one side surface of the first substrate 300a or the second substrate 300b. In this case, the receiver 500 may be variously selected depending on chemical substance to be detected.

Figure 16:
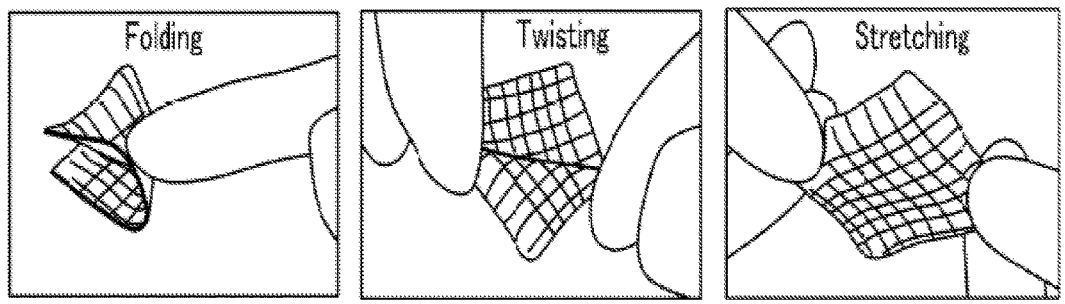
FIG. 16 shows images of the sensing unit of the multimodal sensor manufactured according to an embodiment example.

FIG. 16 shows images of the sensing unit of the multimodal sensor manufactured in accordance with an example embodiment.

Figure 17:
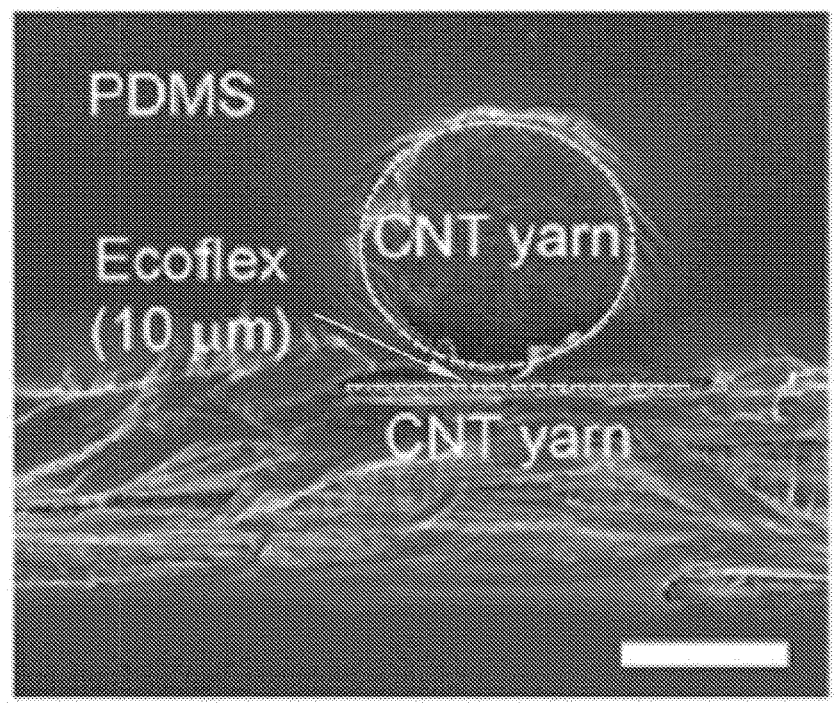
FIG. 17 is an scanning electron microscope image of a cross-section of the sensing unit manufactured in accordance with an example embodiment.

FIG. 17 is an scanning electron microscope image of a cross section of the sensing unit manufactured according to an example embodiment.

Figure 18:
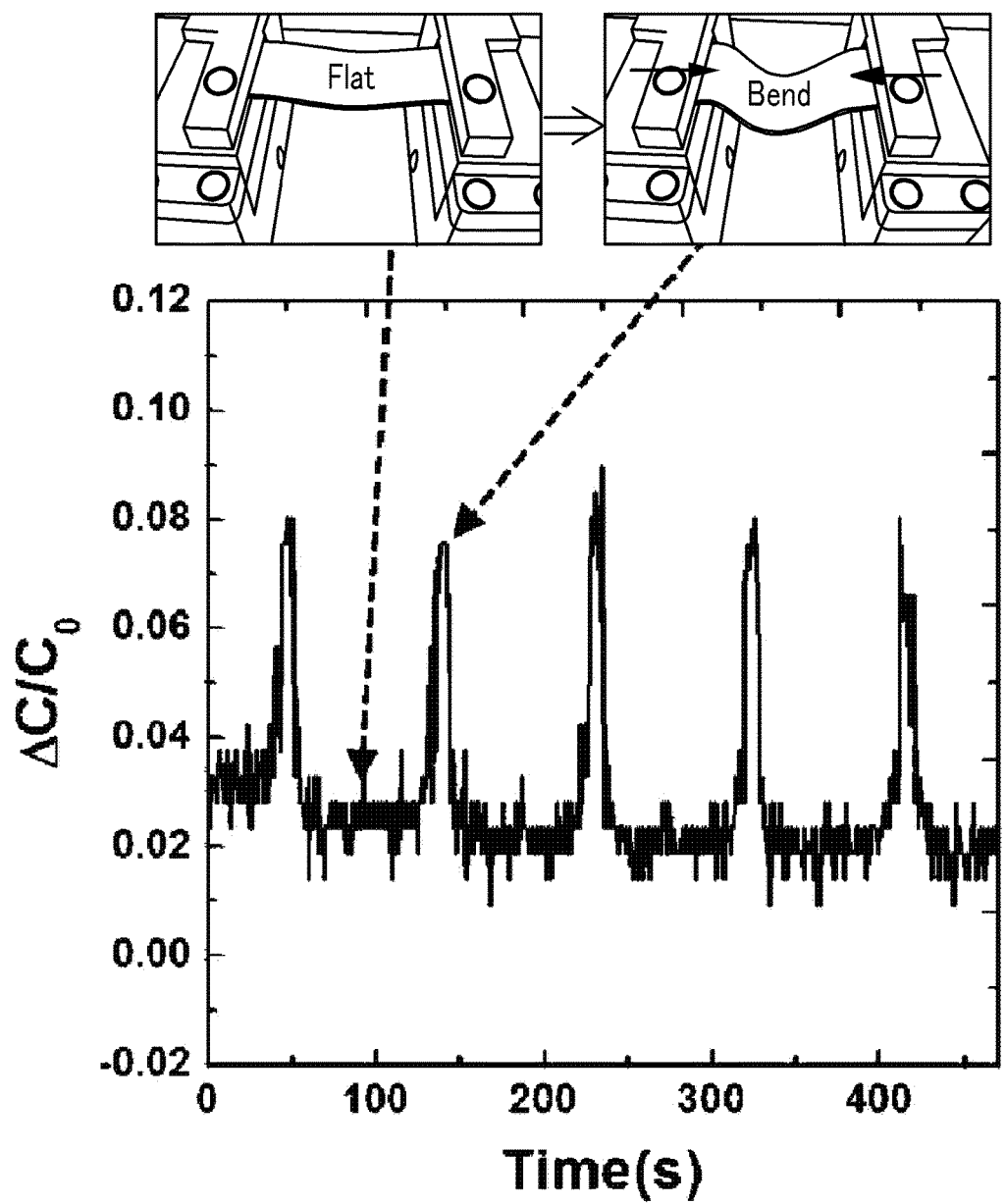
FIG. 18 is a graph for a variation value of capacitance depending on bending change in the sensing unit manufactured in accordance with an example embodiment.

FIG. 18 is a graph for a variation value of capacitance according to bending change in the sensing unit manufactured in accordance with an example embodiment.

As illustrated in FIG. 16 to FIG. 18, the sensing unit 10 of the multimodal sensor manufactured in accordance with an example embodiment can be folded, bent, and twisted, and is flexible. Accordingly, the sensing unit can maintain superior durability against various external physical stresses. Especially, as illustrated in FIG. 18, it can be identified that when the sensing unit 10 of the multimodal sensor manufactured in accordance with an example embodiment is bent, a capacitance value of the sensor increases due to the bending. Specifically, when bending of the multimodal sensor occurs, the capacitance value increases, and when the extent of the bending decreases, the capacitance value also decreases. That is, the multimodal sensor 10 in accordance with an example embodiment senses bending, in addition to a vertical pressure and touch.

Figure 19:
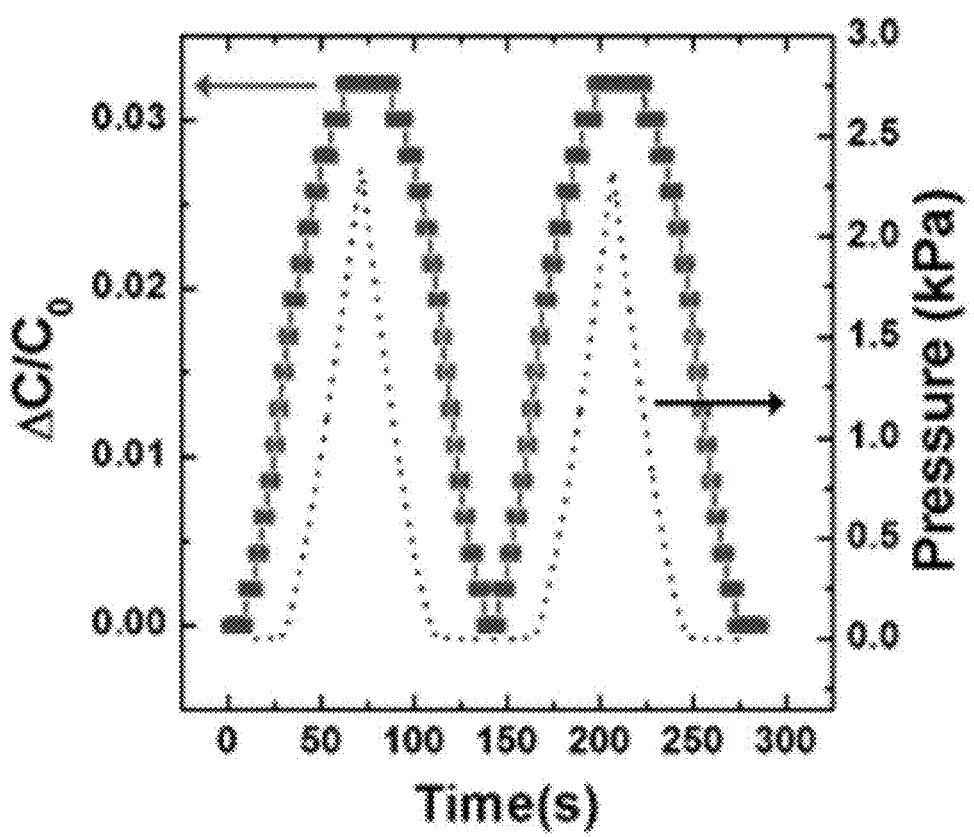
FIG. 19 is a graph for variation of capacitance depending on pressure change in the multimodal sensor manufactured in accordance with an example embodiment.

FIG. 19 is a graph showing variation of capacitance depending on pressure change in the multimodal sensor manufactured in accordance with an example embodiment.

Figure 20:
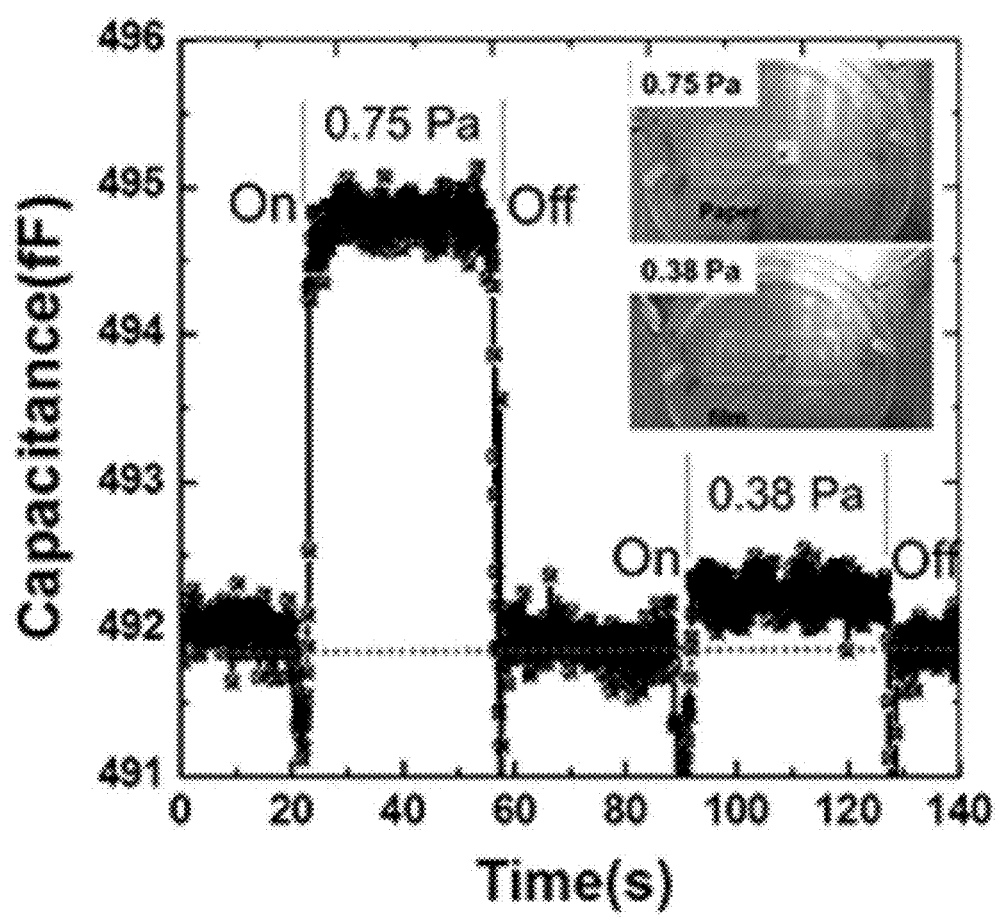
FIG. 20 is a graph for variation of capacitance depending on low pressure change of the multimodal sensor manufactured in accordance with an example embodiment.

FIG. 20 is a graph showing variation of capacitance depending on low pressure change in the multimodal sensor manufactured in accordance with an example embodiment.

Referring to FIG. 19, the multimodal sensor in accordance with an example embodiment has a capacitance value that increases when a pressure increases, and the capacitance value decreases when a pressure decreases.

In addition, referring to FIG. 20, it can be identified that the multimodal sensor manufactured in accordance with an example embodiment sensitively reacts even when a low pressure of about 0.38 Pa is applied.

That is, a capacitance value of the multimodal sensor manufactured in accordance with an example embodiment is proportional to a pressure, and sensitively reacts even at a low pressure. Thus, the multimodal sensor manufactured in accordance with an example embodiment can be applied as a pressure sensor.

Figure 21:
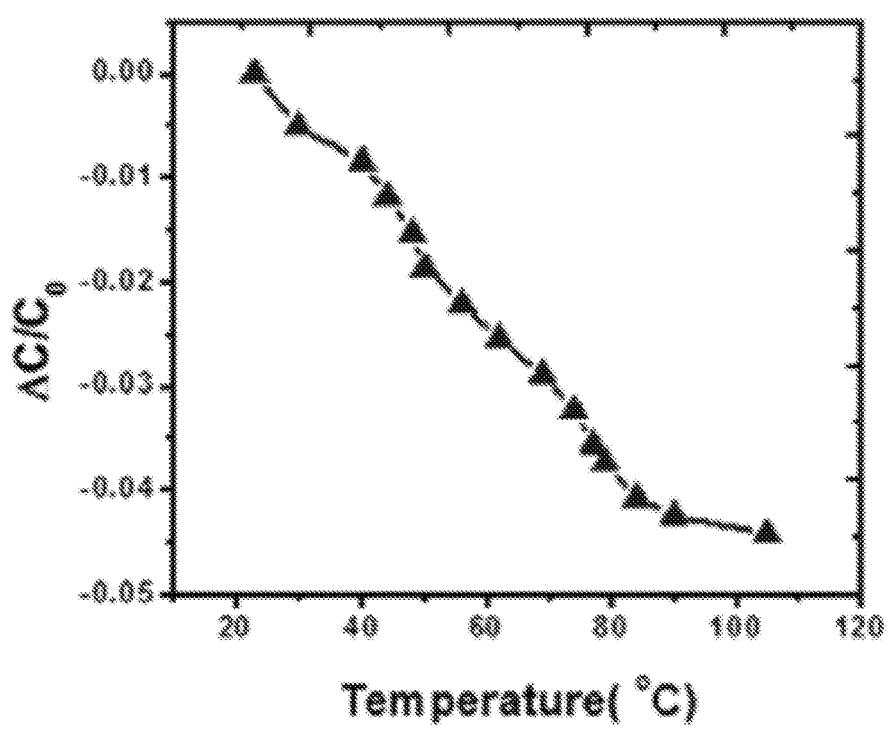
FIG. 21 is a graph for variation of capacitance depending on temperature change in the multimodal sensor manufactured in accordance with an example embodiment.

FIG. 21 is a graph showing variation of capacitance depending on temperature change in the multimodal sensor manufactured in accordance with an example embodiment.

Referring to FIG. 21, it can be identified that in the multimodal sensor in accordance with an example embodiment, a capacitance value linearly decreases as a temperature increases. Thus, the multimodal sensor in accordance with an example embodiment can be applied as a temperature sensor.

Figure 22:
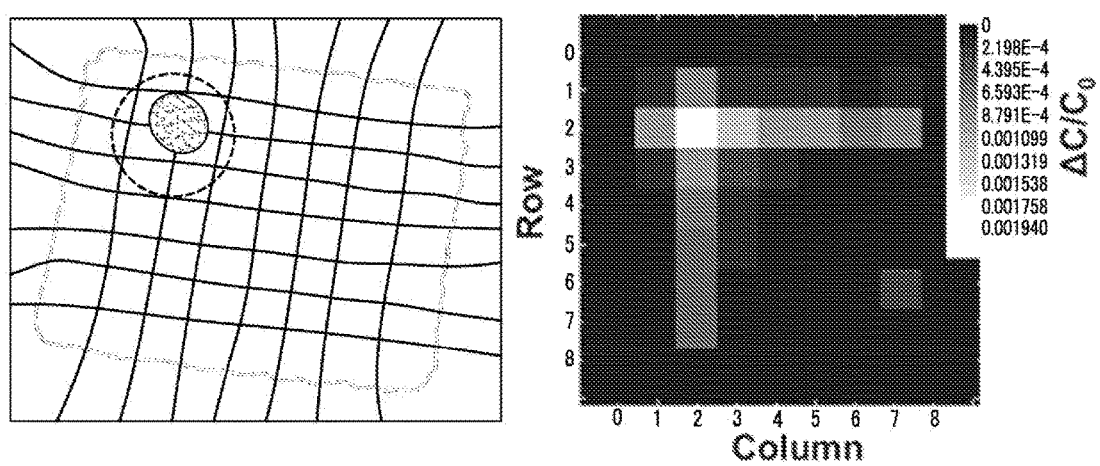
FIG. 22 shows an example embodiment for detecting coordinates of a specific position of the multimodal sensor manufactured in accordance with an example embodiment when a pressure is applied to the position.

FIG. 22 shows an example for detecting coordinates of a specific position, to which a pressure is applied, in the multimodal sensor manufactured in accordance with an example embodiment.

The ladybug illustrated in FIG. 22 weighs 10 mg. FIG. 22 illustrates that it can be identified that a variation value of capacitance at the point where the ladybug having the small weight of 10 mg is present is significant.

In a multimodal sensor 10 manufactured in accordance with another example embodiment, a multiple number of first carbon nanotube fiber electrodes and a multiple number of second carbon nanotube fiber electrodes may be arranged to cross with one another. Accordingly, by measuring a capacitance value at each of points where the first and second carbon nanotube fiber electrodes cross with one another, it is possible to detect x and y coordinates for a position where touch or a pressure is applied, i.e., the position where the ladybug is present. In addition, even if a motion to apply touch or a pressure occurs at a multiple number of points, it is possible to realize a multi-touch function since the points where the electrodes cross with one another are electrically separated.

Figure 23A:
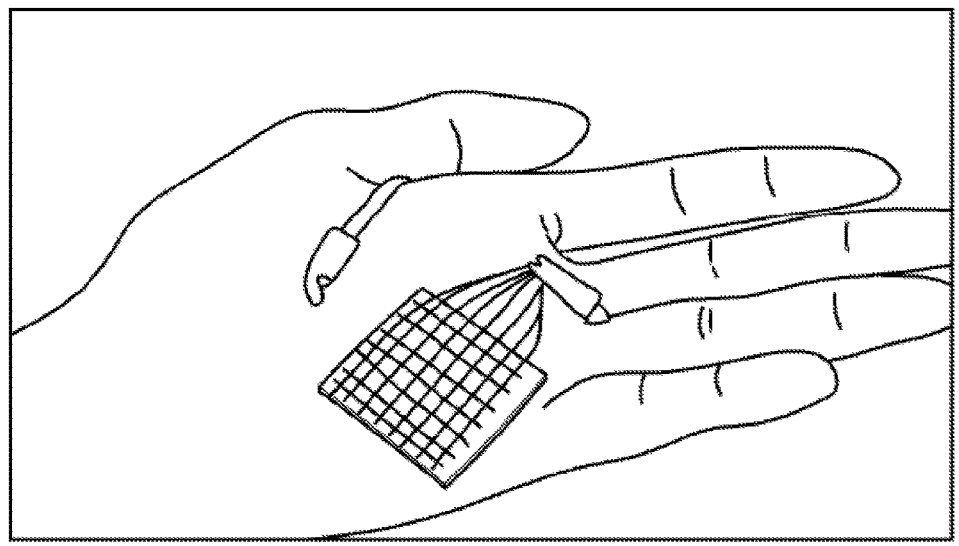
FIGS. 23A, 23B, and 23C show an example embodiment for using the multimodal sensor manufactured in accordance with an example embodiment.
Figure 23B:
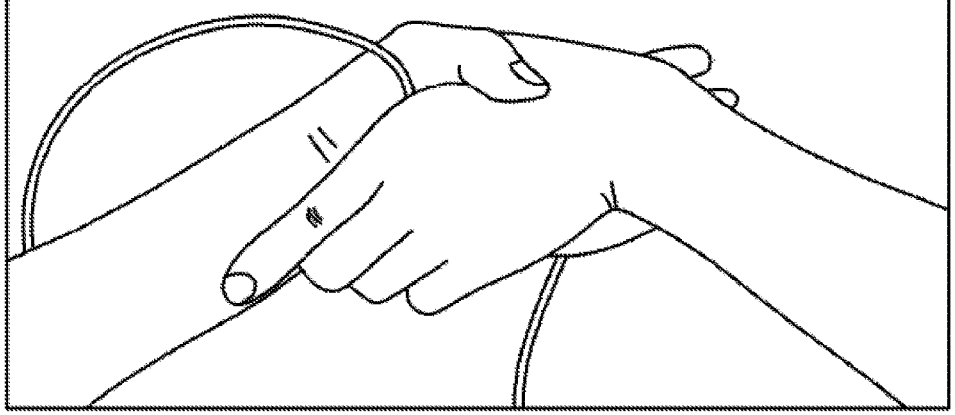
Figure 23C:
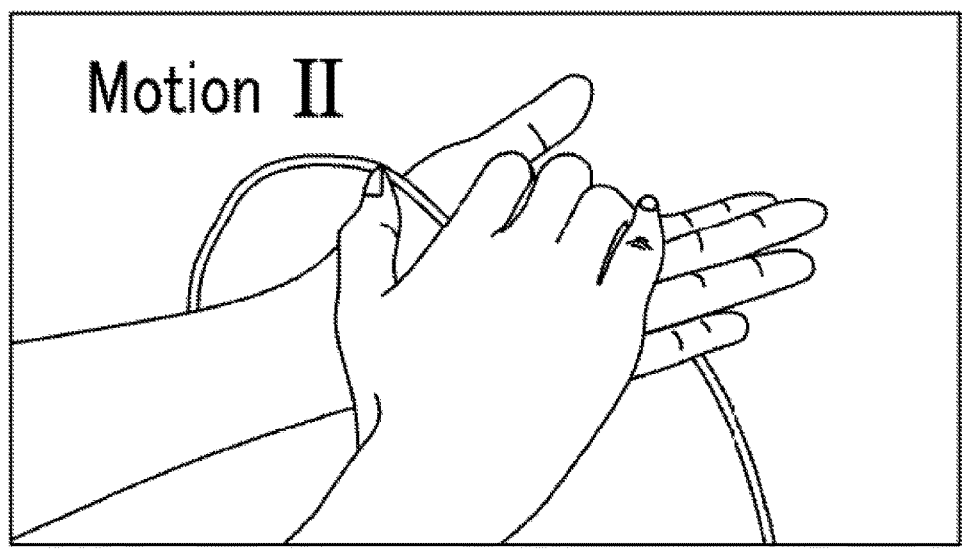

FIGS. 23A-23C show an example for utilizing the multimodal sensor manufactured in accordance with an example embodiment.

FIG. 24 shows an example for detecting the motions of FIGS. 23B and 23C by using the multimodal sensor manufactured in accordance with an example embodiment.

As illustrated in FIGS. 23A-23C, (FIG. 23A) the multimodal sensor manufactured in accordance with an example embodiment was attached onto a person's skin, and variation of capacitance was measured for each of the following motions: (FIG. 23B) when the person with the sensor attached contacts another person with no sensor attached, and (FIG. 23C) the person with the sensor attached contacts his/her hand. In FIG. 24, Motion I (20) shows a capacitance variation value in case of the motion illustrated in FIG. 23B, and Motion II (30) shows a capacitance variation value in case of the motion illustrated in FIG. 23C.

Referring to FIGS. 23A-23C and FIG. 24, in case of the motion of FIG. 23B, a capacitance value decreases until the contact with another person occurs such that a pressure is applied, due to the above-described fringe capacitance effect (22). However, when another hand contacts the sensor such that a pressure is actually applied, the capacitance value increases due to the pressure.

Meanwhile, in case of the motion of FIG. 23C, in which the person with the sensor attached contacts his/her hand, the same phenomenon, i.e., the increase of the capacitance value occurs; however, since the other hand shaking the hand of the person with the sensor attached is connected to the person's body, accomplishing a grounding effect, the fringe effect is offset. Thus, the phenomenon that the capacitance value decreases until a pressure is applied as shown in 22 of FIG. 24 does not occur.

This example embodiment demonstrates that the multimodal sensor in accordance with an example embodiment can be utilized as a motion sensor. If the sensor is applied to robot's skin, the robot can sense a motion of a person approaching the robot in advance to take actions, and also recognize the circumstance that the robot contacts real skin.

In addition to the example embodiment that discriminates motions, since the multimodal sensor in accordance with an example embodiment can sense touch, pressure and temperature change and others by both sides thereof through the first substrate 300a and the second substrates 300b, it is also possible to determine whether a first object touched on the first substrate 300a and a second object touched on the second substrate 300b are identical to each other.

FIG. 25 shows a variation value of capacitance depending on change of a solvent contacting the multimodal sensor manufactured in accordance with an example embodiment.

Figures 26, 27:
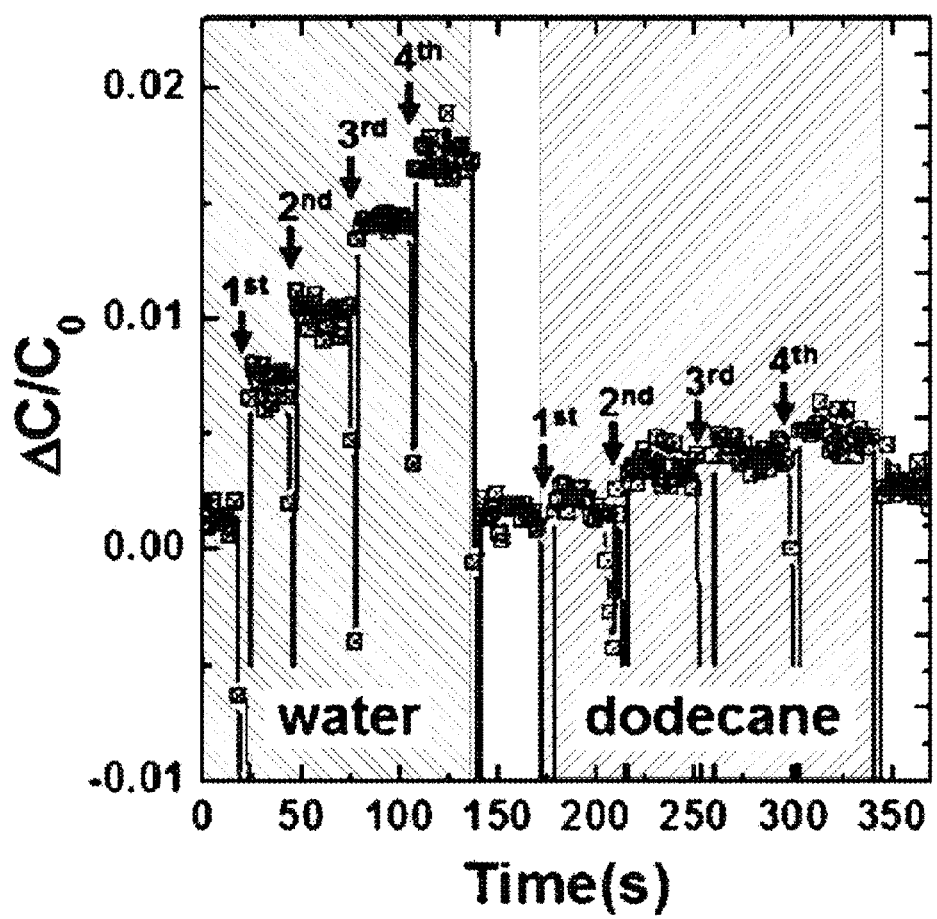
FIG. 26 shows a variation value of capacitance depending on pH change of a solvent contacting the multimodal sensor manufactured in accordance with an example embodiment.
FIG. 27 is a graph for comparison of variation values of capacitance when water and dodecane contact the multimodal sensor manufactured in accordance with an example embodiment.

FIG. 26 shows a variation value of capacitance depending on a pH change of a solvent contacting the multimodal sensor manufactured in accordance with an example embodiment.

Referring to FIG. 25, it can be identified that when solvents having different dipole moments contact the surface of the first substrate 300a or the second substrate 300b of the multimodal sensor manufactured in accordance with an example embodiment under the condition of an identical contact area and identical mass, a capacitance variation value is high as the dipole moment value is high.

In addition, as illustrated in FIG. 26, it can be identified that in the multimodal sensor manufactured in accordance with an example embodiment, capacitance varies depending on a pH value of a solvent contacting the sensor. Specifically, in accordance with an example embodiment, when artificial perspiration and distilled water, which are different in pH from each other, drop on a capacitor-type odor sensor, a variation value of capacitance increases as pH increases, and a variation value of capacitance decreases as pH decreases, based on distilled water having pH of about 7.

FIG. 27 is a graph for comparison of capacitance variation values when water and dodecane contact the multimodal sensor manufactured in accordance with an example embodiment.

Referring to FIG. 27, it can be identified that when water and dodecane, which are significantly different in a dipole moment from each other, contact the multimodal sensor manufactured in accordance with an example embodiment while increasing the water and the dodecane with identical mass, water having a dipole moment of about 1.85 exhibits higher capacitance variation than dodecane having a dipole moment of 0.

Figure 28:
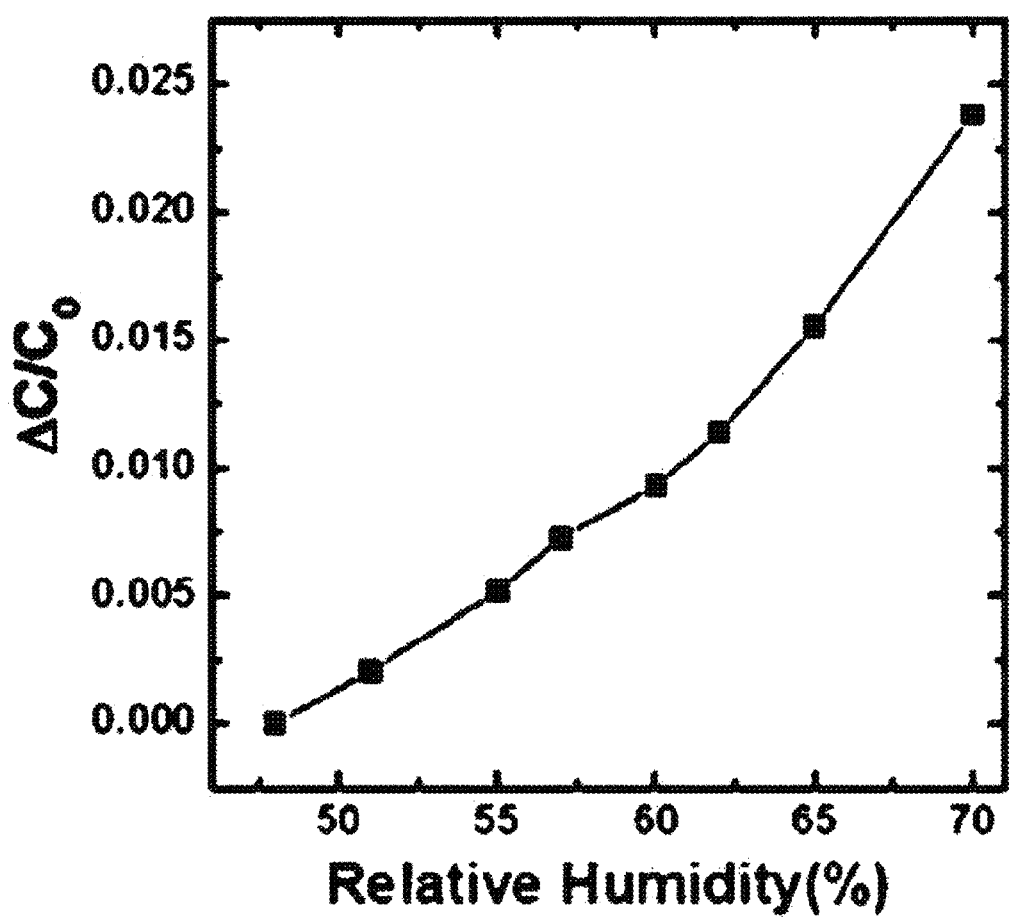
FIG. 28 is a graph for comparison of variation values of capacitance depending on humidity of the multimodal sensor manufactured in accordance with an example embodiment.

FIG. 28 is a graph for comparison of capacitance variation values depending on humidity of the multimodal sensor manufactured in accordance with an example embodiment.

Referring to FIG. 28, it can be identified that a capacitance value of the multimodal sensor manufactured in accordance with an example embodiment constantly increases as a relative humidity value increases. The above-described example embodiment demonstrates that the multimodal sensor in accordance with an example embodiment can sense a specific chemical substance by using a dipole moment value of the chemical substance, and be utilized as a pH sensor as well as a humidity sensor.

Further, the example embodiments can simplify the process for manufacturing the sensor, and manufacture a capacitor-type multimodal odor sensor, which is suitable for a large area, by using a carbon nanotube fiber. Furthermore, it is possible to manufacture a flexible multimodal sensor, which can be folded, bent, and twisted.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

We claim:

1. A multimodal sensor, comprising:
a plurality of first conductive electrodes that are arranged in parallel with one another, being spaced from one another by a distance,
an insulating layer that is formed on the first conductive electrodes,
a plurality of second conductive electrodes that are formed on the insulating layer, crossing the first conductive electrodes, and are arranged in parallel with one another, being spaced from one another,
a first substrate that is formed on a bottom portion of the first conductive electrodes,
a second substrate that is formed on a top portion of the second conductive electrodes, and
a controller that applies voltages to the first and second conductive electrodes,
wherein the controller detects capacitance formed between the first and second conductive electrodes, and senses an external temperature, intensity of a pressure, a position where a pressure is applied or a bending degree of the multimodal sensor, in response to a variation of the capacitance, and
wherein the controller determines whether a first object touched on the first substrate and a second object touched on the second substrate are identical to each other in nature.

2. The multimodal sensor of claim 1,
wherein the capacitance value includes a fringe capacitance component varying depending on presence of a target material to be detected.

3. The multimodal sensor of claim 2,
wherein the controller detects a specific chemical substance present in gas or liquid, by comparing a plurality of pre-stored capacitance variation values and the variation of the capacitance, wherein the pre-stored capacitance variation values are matched with a dipole moment of the each chemical substance.

4. The multimodal sensor of claim 1,
wherein the first and second substrates are any one of polydimethylsiloxane (PDMS), ecoflex, polyurethane (PU), polyethylene phthalate (PET), and polyethylene (PE).

5. The multimodal sensor of claim 1, further comprising
a receiver that is bonded with a specific chemical substance on one side of the first or second substrate.

6. The multimodal sensor of claim 1,
wherein the first or second conductive electrode is formed of a conductive organic•inorganic material.

7. The multimodal sensor of claim 6,
wherein the conductive organic•inorganic material is a carbon nanotube fiber.

8. A multimodal sensor, comprising
a first conductive electrode,
an insulating layer formed on the first conductive electrode,
a second conductive electrode that is formed on the insulating layer, and crosses with the first conductive electrode,
a first substrate that is formed on a bottom portion of the first conductive electrode,
a second substrate that is formed on a top portion of the second conductive electrode, and
a controller that applies voltages to the first and second conductive electrodes,
wherein the controller detects capacitance formed between the first and second conductive electrodes, and senses an external temperature, intensity of a pressure, a position where a pressure is applied or a bending degree of the multimodal sensor in response to a variation of the capacitance, and
wherein the controller determines whether a first object touched on the first substrate and a second object touched on the second substrate are identical to each other in nature.

9. The multimodal sensor of claim 8,
wherein the capacitance value includes a fringe capacitance component varying depending on presence of a target material to be detected.

10. The multimodal sensor of claim 9,
wherein the controller detects a specific chemical substance present in gas or liquid, by comparing a plurality of pre-stored capacitance variation values and the variation of the capacitance, wherein the pre-stored capacitance variation values are matched with a dipole moment of the each chemical substance.

11. The multimodal sensor of claim 8, further comprising
a receiver that is bonded with a specific chemical substance on one side of the first or second substrate.

12. The multimodal sensor of claim 8,
wherein the first and second substrates are any one of polydimethylsiloxane (PDMS), ecoflex, polyurethane (PU), polyethylene phthalate (PET), and polyethylene (PE).

13. The multimodal sensor of claim 8,
wherein the first or second conductive electrode is formed of a conductive organic•inorganic material.

14. The multimodal sensor of claim 13,
wherein the conductive organic•inorganic material is a carbon nanotube fiber.

* * * * *